(12) United States Patent
Reddy et al.

(10) Patent No.: US 7,148,354 B2
(45) Date of Patent: Dec. 12, 2006

(54) PROCESS FOR PREPARATION OF DONEPEZIL

(75) Inventors: Manne Satyanarayana Reddy, Hyderabad (IN); Sajja Eswaraiah, Hyderabad (IN); Mathad Vijayavitthal Thippannachar, Hyderabad (IN); Elati Ravi Rama Chandrashekar, Hyderabad (IN); Podichetty Anil Kumar, Hyderabad (IN); Kolla Naveen Kumar, Hyderabad (IN)

(73) Assignees: Dr. Reddy's Laboratories Limited, Hyderabad (IN); Dr. Reddy's Laboratories, Inc., Upper Saddle River, NJ (US)

( * ) Notice: Subject to any disclaimer, the term of this patent is extended or adjusted under 35 U.S.C. 154(b) by 45 days.

(21) Appl. No.: 10/626,499

(22) Filed: Jul. 24, 2003

(65) Prior Publication Data
US 2004/0143121 A1    Jul. 22, 2004

(30) Foreign Application Priority Data
Jul. 24, 2002   (IN)  .......................... 555/MAS/2002

(51) Int. Cl.
*C07D 211/06*   (2006.01)
(52) U.S. Cl. ...................... 546/206; 546/205; 546/238; 546/324
(58) Field of Classification Search ................ 546/206, 546/205, 238, 342
See application file for complete search history.

(56) References Cited

U.S. PATENT DOCUMENTS 4,895,841 A * 1/1990 Sugimoto et al. ...... 514/212.01
5,606,064 A * 2/1997 Lensky ........................ 546/185
6,649,765 B1 * 11/2003 Vidyadhar et al. ........... 546/185

FOREIGN PATENT DOCUMENTS

WO    WO 97/22584    * 6/1997

OTHER PUBLICATIONS

Sugimoto et al. Shnthesis and anti-acetylcholinesterase . . . Bioorg. Med. Chem. Let. v. 2 *8) p. 871-876 (1992).*
Sam et al. "Reduction products . . . " J. Het. Chem. v.2 (4) p. 366-370 (1965).*
Exhibit A search result for making formula VI.*

* cited by examiner

*Primary Examiner*—Celia Chang
(74) *Attorney, Agent, or Firm*—Robert A. Franks; Edward D. Pergament; Milagros A. Cepeda

(57) ABSTRACT

An efficient process for preparation of donepezil is provided. In one embodiment, the process for preparation of donepezil includes suspending a catalyst, which is palladium metal on carbon and the compound of the structure

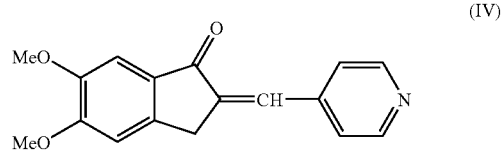

(IV)

in an alcoholic solvent and hydrogenating the suspension at the hydrogen pressure of from about 1 to about 5 and a temperature of from about 40 to about 90° C. till the hydrogenation reaction is substantially complete to obtain a compound of the formula (VI):

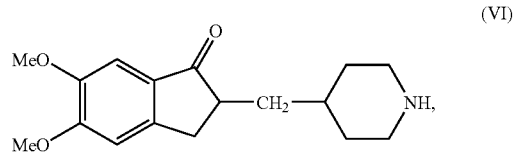

(VI)

which then converted to donepezil. The processes of the invention are believed to be simple, eco-friendly, and commercially viable.

33 Claims, No Drawings

PROCESS FOR PREPARATION OF DONEPEZIL

FIELD OF THE INVENTION

The present invention relates to a process for preparing donepezil.

BACKGROUND OF THE INVENTION

Donepezil, which is chemically known as 2,3-dihydro-5,6-dimethoxy-2[[1-(phenyl methyl)-4-piperidinyl]methyl]-1H-inden-1-one (formula (I)),

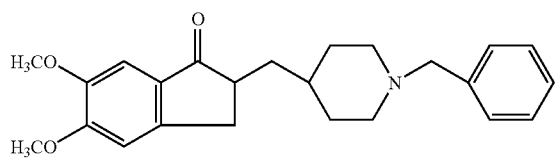

(I)

is useful in the treatment of patients with various conditions involving memory loss, such as senile dementia of Alzheimer's type (DAT).

U.S. Pat. No. 4,895,481, incorporated herein by reference in its entirety, describes donepezil, its related compounds along with their pharmaceutical acceptable salts including composition and method of treatment using them. The process for the preparation of donepezil is disclosed by the aforesaid product patent involves the conversion of 1-benzyl-4-piperidinone to 1-benzyl-4-piperidine carboxaldehyde in the presence of n-butyl lithium, which on further reaction with 5,6-dimethoxy-1-indanone in the presence of strong base such as lithium diisopropylamide under inert atmosphere followed by reduction of the obtained compound to give the title compound of Formula (I) with an overall yield of 27.4%. U.S. Pat. No. 5,606,064, incorporated herein by reference in its entirety, also discloses the process for the preparation of donepezil, which involves reacting 5,6-dimethoxy indanone and pyridine-4-carboxaldehyde to yield 5,6 dimethoxy-2-pyridin-4-yl methylene-indan-1-one, which upon condensation with benzyl bromide followed by reduction of the obtained compound with platinum oxide to afford the title compound with an overall yield of 58.5%. U.S. Pat. No. 6,252,081 B1, incorporated herein by reference in its entirety, also discloses a process for preparation of donepezil (e.g., examples 1, 2, and 3) that provides a satisfactory yield, but utilizes platinum oxide as a reagent. International Application No. WO 97/22584 discloses a process for preparation of donepezil in the (preparations 1–3 and examples 1–6), with an asserted overall yield of 19.3%.

The prior art procedures for the preparation of donepezil have certain disadvantages, such as the use of hazardous raw materials (e.g., lithium diisopropyl amine and n-butyl lithium), costly raw material (e.g., platinum oxide), low temperatures (e.g., –80° C.), a large number of steps, and/or chromatographic separation of intermediates, as well as relatively low yields. Therefore, there is a continuing need for new methods for preparation of donepezil.

SUMMARY OF THE INVENTION

In accordance with one aspect, the invention provides a process for preparation of donepezil which is the compound of the formula (I),

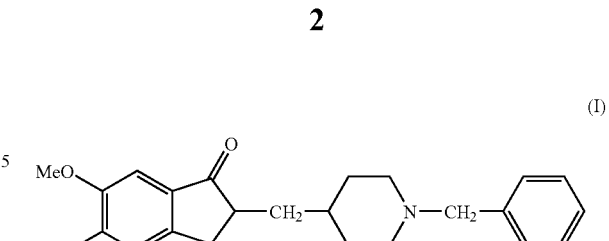

(I)

the process including:
a) suspending a compound of the formula (IV):

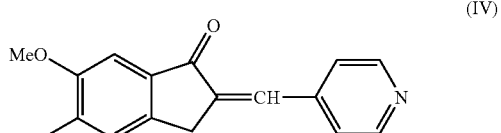

(IV)

and a catalyst, which is palladium metal on a support carrier, in an alcoholic solvent;
b) hydrogenating the suspension at the hydrogen pressure of from about 1 to about 5 and a temperature of from about 40 to about 90° C. till the hydrogenation reaction is substantially complete to obtain a compound of the formula (VI):

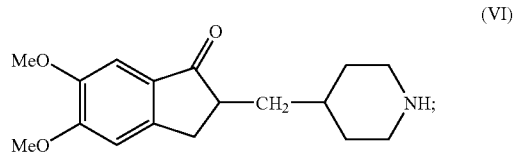

(VI)

c) isolating the compound of formula (VI); and
d) converting the compound of the formula (VI) to the compound of the formula (I).

Specific embodiments and variant of this aspect of the invention are also provided. The processes of the invention are believed to be simple, eco-friendly, and commercially viable.

DETAILED DESCRIPTION OF THE INVENTION

In a preferred embodiment, the present invention relates to an improved and convenient process for the preparation of 2,3-dihydro-5,6-dimethoxy-2[[1-(phenyl methyl)-4-piperidinyl]methyl]-1H-inden-1-one (Donepezil) of the formula (I), which involves a reaction of 5,6-dimethoxy indanone of the formula (II) with pyridine-4-carboxaldehyde of the formula (III) in the presence of an organic solvent to afford 5,6 dimethoxy-2-(pyridin-4-yl)-methylene indan-1-one of the formula (IV). The compound of the formula (IV) is hydrogenated under palladium carbon catalyst in the presence of acetic acid in methanol to afford the acetate salt of the formula (V), which is in situ converted to the key intermediate 5,6-dimethoxy-2-piperidin-4-yl-methyl indan-1-one of the formula (VI). Further reaction of the formula (VI) with benzyl bromide in a solvent in the presence of base yields donepezil of the formula (I) in an overall yield of 83%. The relevant synthetic scheme may be schematically depicted as follows:

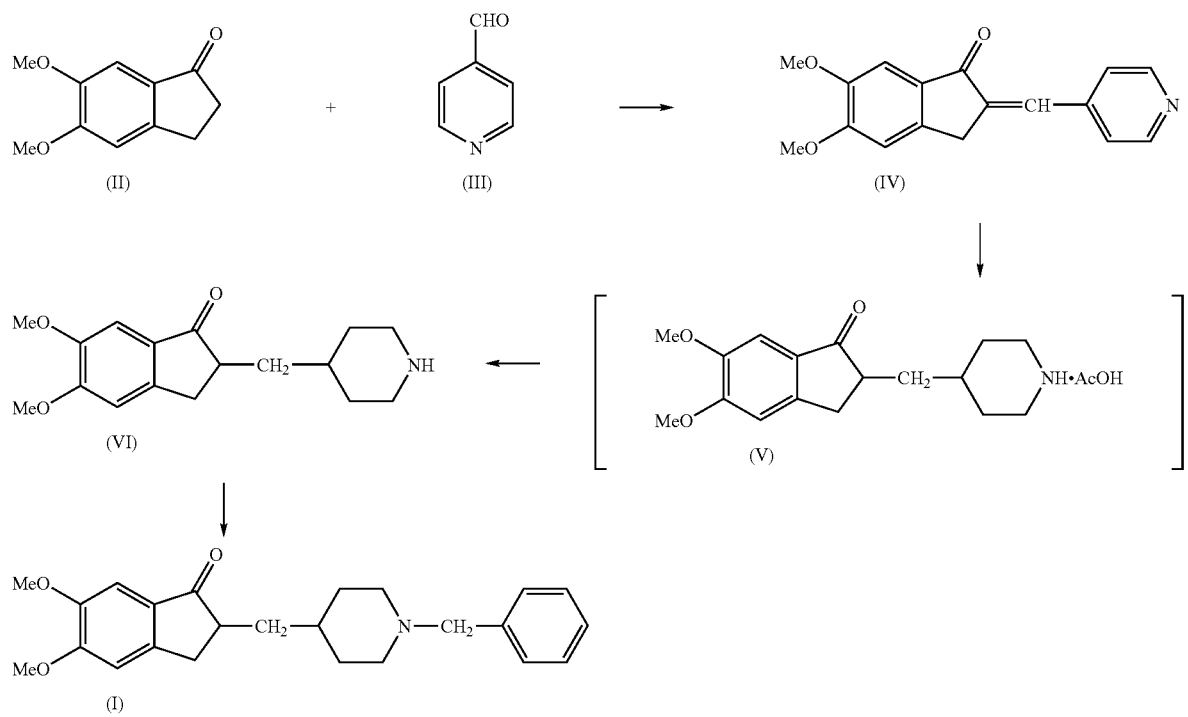

In the preferred embodiment, an improved process for the preparation of donepezil of the formula (I) includes:

a) refluxing the mixture of 5,6-dimethoxy indanone of Formula (II) and pyridine-4-carboxaldehyde of Formula (III) in a solvent such as toluene using p-toluene sulfonic acid as a catalyst till reaction substantially completes;

b) cooling the reaction mixture of step (a) to ambient temperature accompanied by filtering the solid;

c) suspending the solid obtained in step (b) in aqueous basic solutions comprising of sodium hydroxide, sodium carbonate, sodium bicarbonate, potassium hydroxide, potassium carbonate or potassium bicarbonate, preferably aqueous sodium bicarbonate solution followed by stirring for 1–2 hours;

d) filtering the solid obtained in step (c) to afford 5,6 dimethoxy-2-(pyridin-4-yl)-methylene indan-1-one of Formula (IV);

e) suspending the compound of Formula (IV) and Palladium on carbon in alcoholic solvent comprising of methanol, ethanol, n-propanol, isopropanol, n-butanol or tertiary butanol, preferably methanol in presence of acetic acid in hydrogenation vessel;

f) heating the reaction mixture of step (e) under 1–5 atmospheric hydrogen pressure at a temperature of 40 to 90° C., preferably at a temperature of 60–65° C. till the reaction substantially completes;

g) cooling of the reaction mass of step (f) to ambient temperature followed by filtering the catalyst;

h) distilling the solvent from the filtrate obtained in step (g) to get the residue;

i) dissolving the residue obtained in step (h) in water and followed by washing with a chloro solvent comprising of dichloromethane, dichloroethane, chloroform or carbon tetrachloride, preferably dichloromethane and separating the aqueous layer;

j) adjusting the pH of the aqueous layer of step (i) to 9 to 14 with a base solution comprising of sodium hydroxide, sodium carbonate, sodium bicarbonate, potassium hydroxide, potassium carbonate or potassium bicarbonate, preferably aqueous potassium hydroxide solution;

k) extracting the compound from the basified aqueous layer of step (j) with an organic solvent comprising of dichloromethane, chloroform, dichloroethane, toluene, ethyl acetate, isopropyl ether, methyl tertiary butyl ether, diethyl ether or petroleum ether, preferably dichloromethane;

l) distilling the solvent from the reaction solution of step (k) followed by triturating the residue in non-polar organic solvents comprising of n-hexane, n-heptane, cyclohexane, cyclo heptane or petroleum ether, preferably petroleum ether or ether solvents comprising of di ethyl ether, di isopropyl ether, di isobutyl ether or methy tertiary butylether to afford 5,6-dimethoxy-2-piperidin-4-yl methyl-indan-1-one of Formula (VI);

m) reacting the compound of Formula (VI) with benzyl bromide in alcoholic solvents comprising of methanol, ethanol isopropanol, butanol or ketone solvents comprising of acetone, ethylmethyl ketone, 2-butanone in the presence of a base inorganic base comprising of sodium carbonate, sodium bicarbonate, potassium carbonate or potassium bicarbonate or organic base comprising of triethyl amine, tributyl amine, tertiary butyl amine or pyridine at a temperature of 30–80° C., preferably at 50° C. till the reaction substantially completes;

n) cooling the reaction mass to ambient temperature and followed by filtering the mass;

o) diluting the filtrate obtained in step (n) with water and further extracting the compound into ether solvents comprising isopropyl ether, methy tertiary butylether or diethyl ether or aromatic hydrocarbon solvents comprising of toluene, benzene, ethyl benzene, xylene, preferably toluene or aliphatic hydrocarbon solvents comprising of hexane, cyclohexane or petroleum ether.

p) distilling the solvent from the reaction solution of step (o) followed by triturating the residue in non-polar organic solvents comprising of n-hexane, n-heptane, cyclohexane, cyclo heptane or petroleum ether, preferably petroleum ether or ether solvents comprising of di ethyl ether, di isopropyl ether, di isobutyl ether or methy tertiary butylether to afford the title compound Donepezil of Formula (I).

The strength of aqueous base solution mentioned in step c) of the above process is varied from 5 to 20%, preferably 10% w/v of aqueous sodium carbonate solution. The reduction of compound of Formula (IV) mentioned in the step (e) of the above process has done using 5% or 10% Palladium over charcoal to result the acetate salt of Formula (V) in 100% yield, which in situ is converted to the key intermediate of Formula (VI). The strength of aqueous base solution mentioned in step (O) of the above process is varied from 5 to 20%, preferably 10% w/v of aqueous potassium hydroxide solution. Hence the present invention provides a cost effective and eco friendly process, which involves the usage of Palladium carbon instead of Platinum oxide for reduction of compound of Formula (IV), followed by condensation with benzyl bromide to afford Donepezil.

The process of present invention also avoids the usage of hazardous raw materials, such as n-Butyl lithium, phosphorous pentoxide, lithium diisopropylamine (LDA) as mentioned in the prior art. Donepezil obtained in the above process has high purity with up to 92% overall yield.

The invention will be explained in more detail with reference to the following examples, which are provided by way of illustration only and should not be constructed as limit to the scope of the reaction in any manner.

EXAMPLE 1

Preparation of 5,6 Dimethoxy-2-(pyridine-4yl)-methylene-indan-1 one (Compound of the Formula IV)

5,6 Dimethoxy indanone (100 grams), Pyridine-4-carboxaldehyde (78.0 grams) and p-toluene sulfonic acid (138.4 grams) were suspended in toluene (1250 ml) and heated to reflux using water separator for 6 hours. The resulting mass was cooled to 25–40° C. and the solid was filtered off under suction. Further the wet solid was suspended in aqueous 10% sodium carbonate solution (1200 ml) and stirred for 30–60 minutes. The resulting pale yellow precipitate solid was filtered off under suction, washed with water (1000 ml) and dried at a temperature of 80° C. to afford 5,6 Dimethoxy-2-(pyridin-4yl)-methylene-indan-1one (Weight: 140 grams, 95.8%).

EXAMPLE 2

Preparation of 5,6-Dimethoxy-2-piperidin-4-yl methyl-indan-1-one (the Compound of the Formula (VI))

5,6-Dimethoxy-2-(pyridin-4-yl) methylene indan-1-one (IV, 50.0 grams), 5% palladium on activated carbon (12.5 grams), acetic acid (12.8 grams) and Methanol (875 ml) were taken in 2.0 liter hydrogenation flask and applied hydrogen gas in inert atmosphere. The hydrogenation was carried out at hydrogen pressure of 3–4 atmospheres at 60–65° C. for 8 hours. Then the flask was cooled to room temperature and the catalyst was filtered off. The solvent was distilled off from the filtrate and resulting residue was dissolved in water (1000 ml). The aqueous solution thus obtained was washed with Dichloromethane. Further, the pH of the aqueous layer was adjusted to ~13.0 and extracted the compound into Dichloromethane. The combined dichloromethane layer was dried over sodium sulfate and concentrated under vacuum to get the residue. Thus resulted residue was triturated petroleum ether to afford 5,6 Dimethoxy-2-piperidinyl-4-yl methyl-indan-1one (Weight: 49 grams, 95.3%).

EXAMPLE 3

Preparation of 2,3-dihydro-5,6-dimethoxy-2[[1-(phenyl methyl)-4-piperidinyl]methyl]-1H-inden-1-one (Donepezil))

5,6 Dimethoxy-2-piperidinyl-4-yl methyl indan-1-one (VI, 20 grams) was suspended in ethanol (300 ml) and stirred at a temperature of 50° C. to get the clear solution. Sodium carbonate (4.40 grams), Benzyl Bromide (11.8 grams) was added slowly drop wise at a temperature of 50° C. Then, the reaction mass was stirred at a temperature of 55–60° C. for 6 hours and cooled the mass to room temperature. The reaction mass was filtered off and water (300 ml) was added to the filtrate. The compound was extracted from the resulting aqueous solution using toluene (250 ml). The toluene layer was concentrated under vacuum to get the residue. The residue was triturated in petroleum ether to afford the title compound. (Weight: 24.2 grams, 92.3%).

Unless stated to the contrary, any use of the words such as "including," "containing," "comprising," "having" and the like, means "including without limitation" and shall not be construed to limit any general statement that it follows to the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

What is claimed is:

1. A process for preparation of donepezil which has the formula (I),

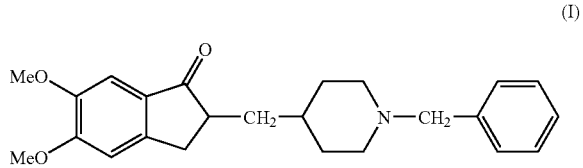

(I)

said process comprising:
a) suspending a compound of the formula (IV):

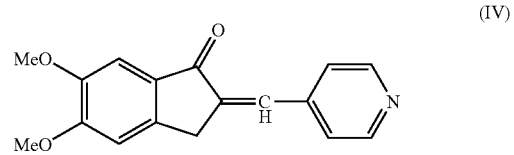

(IV)

and a catalyst, which is palladium metal on a support carrier, in an alcoholic solvent;

b) hydrogenating the suspension at the hydrogen pressure of from about 1 to about 5 atmospheres and a temperature of from about 40 to about 90° C. until the hydrogenation reaction is substantially complete to obtain a compound of the formula (VI):

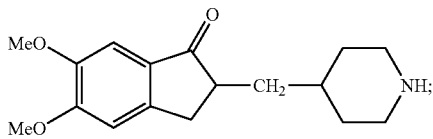

c) isolating said compound of formula (VI); and
d) converting said compound of the formula (VI) to said compound of the formula (I).

2. The process of claim 1, wherein said step of isolating said compound of the formula (VI) includes c.1) removing the palladium catalyst;
c.2) removing the alcoholic solvent to obtain a residue;
c.3) contacting said residue with water to obtain an aqueous solution of said residue;
c.4) adjusting the pH of said aqueous solution to a range of from about 9 to about 14;
c.5) contacting said aqueous solution having said adjusted pH with an organic extractant;
c.6) separating said organic layer containing said residue; and
c.7) distilling said extractant from said organic layer thereby obtaining a second residue of the compound of the formula (VI).

3. The process of claim 2, further comprising triturating the second residue in a non-polar organic solvent selected from the group consisting of n-hexane, n-heptane, cyclohexane, cycloheptane, diethyl ether, diisopropyl ether, diisobutyl ether, methyl tertiary butyl ether, and petroleum ether.

4. The process of claim 1, wherein said alcoholic solvent is selected from the group consisting of methanol, ethanol, n-propanol, isopropanol, n-butanol and tertiary butanol.

5. The process of claim 1, further comprising hydrogenating in the presence of acetic acid.

6. The process of claim 5, wherein said alcoholic solvent is methanol.

7. The process of claim 1, wherein said hydrogenation temperature is from about 60 to about 65° C.

8. The process of claim 2, wherein said extractant is selected from the group consisting of dichloromethane, dichloroethane, chloroform and carbon tetrachloride.

9. The process of claim 2, wherein said pH is adjusted with a aqueous solution of a base selected from the group consisting of sodium hydroxide, sodium carbonate, sodium bicarbonate, potassium hydroxide, potassium carbonate and potassium bicarbonate.

10. The process of claim 1, wherein said step of converting the compound of the formula (IV) to the compound of the formula (I) includes reacting the compound of the formula (VI) with benzyl bromide in a second alcoholic solvent in the presence of a second base at a temperature of from about 30 to about 80° C.

11. The process of claim 10, wherein said second alcoholic solvent is selected from the group consisting of methanol, ethanol isopropanol, butanol acetone, ethylmethyl ketone, and 2-butanone.

12. The process of claim 10, wherein said second base is selected from the group consisting of sodium carbonate, sodium bicarbonate, potassium carbonate and potassium bicarbonate.

13. The process of claim 10, wherein said second base is selected from the group consisting of triethyl amine, tributyl amine, tertiary butyl amine and pyridine.

14. The process of claim 10, further comprising cooling the reaction mass to ambient temperature, filtering the reaction mass, diluting the filtrate with water and contacting the aqueous mixture with a second organic extractant.

15. The process of claim 14, wherein said second organic extractant is selected from the group consisting of isopropyl ether, methyl tertiary butyl ether, diethyl ether, toluene, benzene, ethyl benzene, xylene, hexane, cyclohexane and petroleum ether.

16. The process of claim 15, further comprising separating the organic layer and removing said second organic extractant therefrom to obtain a third residue.

17. The process of claim 16, further comprising triturating said third residue in a non-polar organic solvent selected from the group consisting of n-hexane, n-heptane, cyclohexane, cycloheptane, diethyl ether, diisopropyl ether, diisobutyl ether, methyl tertiary butyl ether, and petroleum ether.

18. The process of claim 1, further comprising reacting a compound of the formula (II)

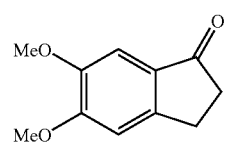

with a compound of the formula (III)

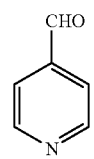

to obtain said compound of the formula (IV).

19. A process for preparation of donepezil, said process comprising:

a. refluxing a mixture of 5,6-dimethoxy indanone of the formula (II)

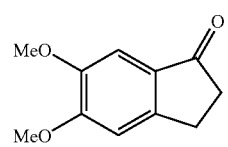

and pyridine-4-carboxaldehyde of the formula (III)

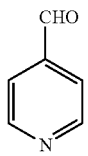

(III)

in toluene in the presence of p-toluene sulfonic acid until the reaction is substantially complete thereby a solid is formed;

b. cooling the reaction mixture to ambient temperature and filtering the solid;
c. suspending the filtered solid in an aqueous basic solution and stirring the suspension;
d. filtering the solid obtained in step c. to afford 5,6 dimethoxy-2(pyridin-4-yl)-methylene indan-1-one of the formula (IV):

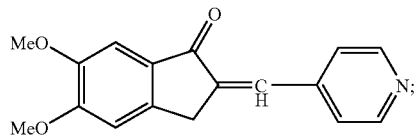

(IV)

e. suspending the compound of the formula (IV) and palladium on carbon in an alcoholic solvent selected from the group consisting of methanol, ethanol, n-propanol, isopropanol, n-butanol and tertiary butanol in the presence of acetic acid in a hydrogenation vessel;
f. heating the reaction mixture of step e. under 1–5 atmospheres hydrogen pressure at a temperature of 40 to 90° C. until the reaction substantially completes;
g. cooling of the reaction mass of step f. to ambient temperature followed by filtering the catalyst;
h. distilling the solvent from the filtrate obtained in step g. to get a residue;
i. dissolving the residue obtained in step h. in water and followed by washing with a chloro solvent selected from the group consisting of dichloromethane, dichloroethane, chloroform and carbon tetrachloride, and separating the aqueous layer;
j. adjusting the pH of the aqueous layer of step i. to 9 to 14 with a base solution comprising of sodium hydroxide, sodium carbonate, sodium bicarbonate, potassium hydroxide, potassium carbonate or potassium bicarbonate;
k. extracting the compound from the basified aqueous layer of step j. with an organic solvent selected from the group consisting of dichloromethane, chloroform, dichloroethane, toluene, ethyl acetate, isopropyl ether, methyl tertiary butyl ether, diethyl ether and petroleum ether;
l. distilling the solvent from the reaction solution of step k., followed by triturating the residue in a non-polar organic solvent selected from the group consisting of n-hexane, n-heptane, cyclohexane, cyclo heptane, di ethyl ether, di isopropyl ether, di isobutyl ether, methyl tertiary butylether and petroleum ether, to afford 5,6-dimethoxy-2-piperidin-4-yl methyl-indan-1-one of the formula (VI):

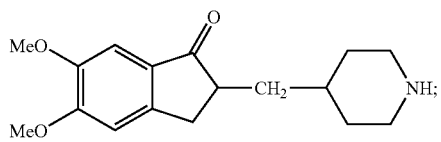

(VI)

m. reacting the compound of the formula (VI) with benzyl bromide in a solvent selected from the group consisting of methanol, ethanol isopropanol, butanol acetone, ethylmethyl ketone, and 2-butanone in the presence of a base selected from the group consisting of sodium carbonate, sodium bicarbonate, potassium carbonate, potassium bicarbonate, triethyl amine, tributyl amine, tertiary butyl amine and pyridine at a temperature of 30–80° C., until the reaction substantially completes;
n. cooling the reaction mass to ambient temperature and followed by filtering the mass;
o. diluting the filtrate obtained in step n. with water and further extracting the compound into ether solvents selected from the group consisting of isopropyl ether, methy tertiary butylether, diethyl ether, toluene, benzene, ethyl benzene, xylene, hexane, cyclohexane and petroleum ether; and
p. distilling the solvent from the reaction solution of step o. followed by triturating the residue in a non-polar organic solvent selected from the group consisting of n-hexane, n-heptane, cyclohexane, cyclo heptane, di ethyl ether, di isopropyl ether, di isobutyl ether, methyl tertiary butylether and petroleum ether, to obtain the donepezil of the formula (I):

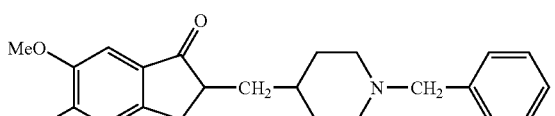

(I)

20. The process of claim 19, wherein said aqueous basic solution of step c. is a solution of sodium hydroxide, sodium carbonate, sodium bicarbonate, potassium hydroxide, potassium carbonate or potassium bicarbonate.

21. The process of claim 19, wherein said aqueous basic solution of step c. is 10% w/v sodium bicarbonate solution.

22. The process of claim 19, wherein the catalyst for catalytic hydrogenation of step e. is 5% or 10% palladium over carbon.

23. The process of claim 19, wherein the catalyst for catalytic hydrogenation of step e. is carried out in the presence of 1 to 5 mole ratio of acetic acid with respect to the compound of the formula (IV).

24. The process of claim 23, wherein said mole ratio is 1.0 to 1.5.

25. The process of claim 1, wherein said carrier is carbon.

26. The process of claim 19, wherein the chloro solvent of step i. is dichloromethane.

27. The process of claim 19, wherein the aqueous base solution of step j. is 10% w/v potassium hydroxide solution.

28. The process of claim 19, wherein the non-polar solvent for trituration of step l. is petroleum ether.

29. The process of claim 19, wherein said alcoholic solvent of step (m) is ethanol.

30. The process of claim 19, wherein the inorganic base of step m. is sodium carbonate.

31. The process of claim 19, wherein the reaction temperature of step m. is 55–60° C.

32. The process of claim 19, wherein the aromatic hydrocarbon solvent of step o. is toluene.

33. The process of claim 19, wherein the non-polar solvent for trituration of step p. is petroleum ether.

* * * * *